US00PP09316P

United States Patent [19]

Zerr

[11] Patent Number: Plant 9,316

[45] Date of Patent: Oct. 3, 1995

[54] POINSETTIA PLANT NAMED 'FISBLA'

[75] Inventor: Katharina Zerr, Simmern, Germany

[73] Assignee: Florfis AG, Binningen, Switzerland

[21] Appl. No.: 328,053

[22] Filed: Oct. 24, 1994

[30] Foreign Application Priority Data

Dec. 29, 1993 [DE] Germany ..... EUP 148

[51] Int. Cl.[6] ..... A01H 5/00

[52] U.S. Cl. ..... Plt./86.1

[58] Field of Search ..... Plt./86.1, 86.4

[56] References Cited

U.S. PATENT DOCUMENTS

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of poinsettia plant named Fisbla, characterized by the combined traits of light pink bracts with broad white margin, medium height, compact and bushy plant habit, medium green foliage, and medium early flowering response.

2 Drawing Sheets

Fisbla is a product of a mutation induction program carried out by the inventor in Hillscheid, Germany in 1991. The primary object of the induction program was to expand the bract color ranges of Peterstar, disclosed in U.S. Plant Pat. No. 8,259, and characterized by its bright red bract color, medium green foliage, comparatively compact plant habit, medium early response in autumn, and good branching ability.

The irradiation program resulting in the new cultivar comprised exposing rooted cuttings taken from plants of the parent cultivar to an X-ray source in Ahrensburg, Germany under the supervision of the inventor. The dosage was 30 Gy. The irradiated plants were grown out in a greenhouse in Hillscheid, Germany and were asexually propagated by taking cuttings. These cuttings were grown outdoors near Galdar, Gran Canaria, Spain, under the supervision of the inventor. Parts of plants showing mutation were cut from the remainder of the plants by the inventor and planted as cuttings. The plants grown from these cuttings were identified by the number and selections were made by the inventor in autumn 1991.

The new cultivar evolved from a flowering branch of an irradiated plant in which part of the bracts showed pink or pink and white coloring. The mutated branch was designated No. 135 and was grown out and propagated several times by cuttings by the inventor in Hillscheid, Germany in order to eliminate unstable/partial chimera and select this specific chimera to obtain a plant with stable and uniform characteristics.

Horticulture examination initiated in 1992 and continuing thereafter has demonstrated that the combination of characteristics as herein disclosed for Fisbla are firmly fixed and are retained through successive generations of asexual reproduction.

The following traits have been repeatedly observed and are determined to be basic characteristics of Fisbla which in combination distinguish this poinsettia as a new and distinct cultivar:

1. Light pink bracts with broad white margin.
2. Medium plant height.
3. Compact and bushy.
4. Medium Green foliage.
5. Medium early flowering response.

Fisbla has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

In comparison to the sibling variety Fispue, obtained from the same induced mutation program and also having pink and white variegated bracts, the marginal white are of Fisbla is far more distinct. The central pink part of Fisbla is slightly marbled and there are lighter and darker pink spots (RHS 51B and 51C), lighter pink (RHS 51C) in color. Further, the foliage of Fisbla has a more intense green color, its bracts are almost ovate in shape (the bracts of Fispue are larger and elliptical in shape) and rugose in texture, compared to the comparatively smooth bract surface of Fispue.

In comparison to the commercial but unpatented cultivar Marbella, Fisbla grows less vigorously and has a more compact growth habit. The coloring of the bracts of Fisbla is more distinct and intense, with the white margin being much broader. The bracts of Fisbla are imbricated, almost ovate with long tips and form a close involucre with a narrow center. The bracts of Marbella are weakly imbricated, and shorter with a wedge shaped base and larger petioles whereby the middle of the involucre looks wider. Also, the bracts and cyathia of Marbella mature later.

Compared to Peterstar, Fisbla has light pink and white bracts, whitish green leaf venation, somewhat darker foliage, and a taller plant height.

The accompanying color photographic drawings show typical inflorescence and foliage of Fisbla, with colors being as true as possible with illustrations of this type.

In the photograph on Sheet 1, a typical mature potted plant of Fisbla appears on the left and a mature potted plant of comparison cultivar Marbella appears on the right, with the bract colors not being accurately depicted.

The photo or Sheet 2 is of a single plant of Fisbla, with the darker and lighter pink bract color accurately being depicted.

In the following description, color references are made to The Royal Horticultural Society Colour Chart. The color values were determined indoors in a north light. The plants described were grown in Hillscheid, Germany (latitude 50° N). They were planted as rooted cuttings into 14 cm pots in early August, potted in late-August and pinched 10 days later. Plants were lighted (long day conditions) from mid-September. From October 1, the plants were grown in a greenhouse under natural short day conditions at 18° C. night temperature and 18° to 24° C. day temperature. Observations and measurements were taken at the beginning of flowering when three (3) cyathias were open.

Classification:

*Botanical.—Euphorbia pulcherrima.*

*Commercial.*—Poinsettia, cv. Fisbla.

Parentage: Induced mutation of Peterstar.

Plant description:

*Form.*—Bushy but somewhat narrow plant habit; 8–9 branches.

*Growth habit.*—Medium height: 30–35 cm.

*Rooting.*—Fast, less than 20 days.

*Blooming season.*—From early December (about 9–10 weeks of response time).

*Blooming habit.*—Marketable in early December when 3–6 bracts are colored.

*Foliage.*—Size: Leaf is approximately 12–13 cm in length; petiole is 8.5 cm in length. Internodes: 15–20 mm. Color: New Foliage: Upper surface, medium green, between 143A and 144A; under surface 144A. Old Foliage: Upper surface, medium to dark green 139A; under surface 137C. Leaf Petiole: Light green. Shape: Broad, elliptical with very weak lobes, rounded base. Texture: Upper side, weak rugosity; lower side, weak veins. Edge of margin: Entire. Disease resistance: None observed.

Flowering description:

*Cyathias.*—Borne: In a narrow cluster. Quantity: 20–24. Retention: Good.

*Bracts.*—Ovate, with long tips, rounded base, and short petioles; surface has comparatively strong rugosity; largest colored bract with petiole is 17 cm long.

*Color.*—Pink and lighter pink, becoming white near margin, with the margin being irregular; young bracts are closest in main color to 51B, becoming when mature 51C; lighter pink color is approximately 51D.

*Aspect.*—Horizontal.

Reproductive organs:

*Glands, nectar cups.*—Yellow.

*Stamens.*—Light brown, hardly fertile stamens.

*Pollen.*—No pollen.

*Styles.*—Whitish, 6-lobed stigma.

*Ovaries.*—Triangular, 3-celled, 3 ovules.

I claim:

1. A new and distinct poinsettia plant named Fisbla, as illustrated and described.

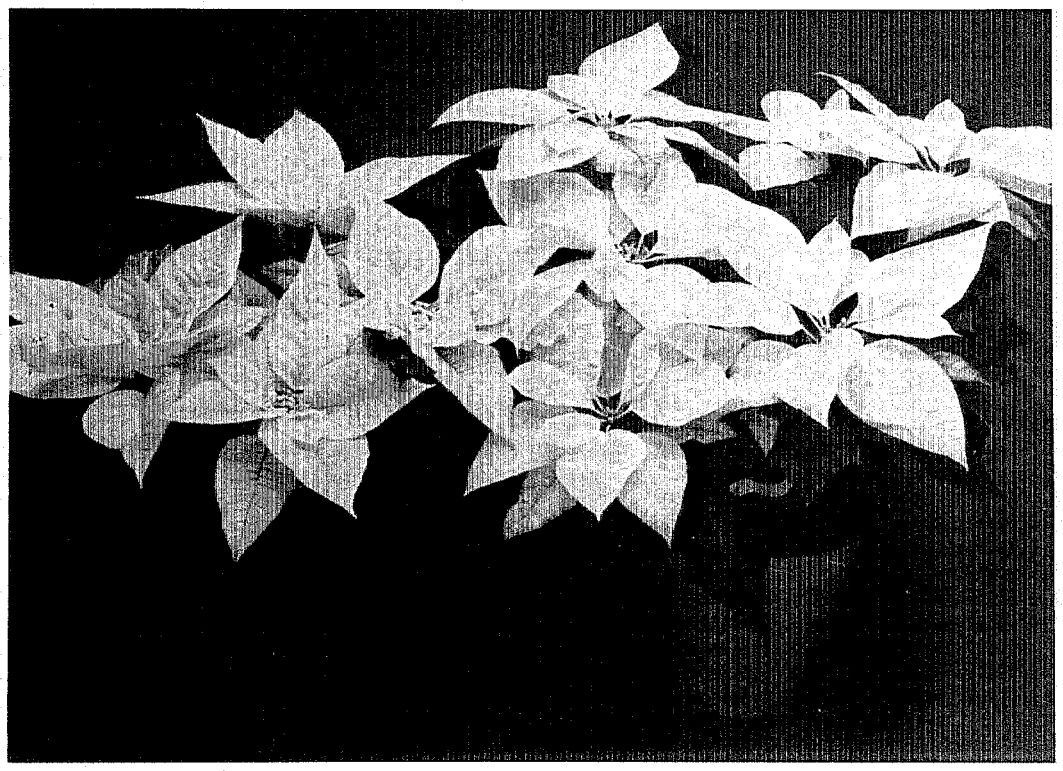

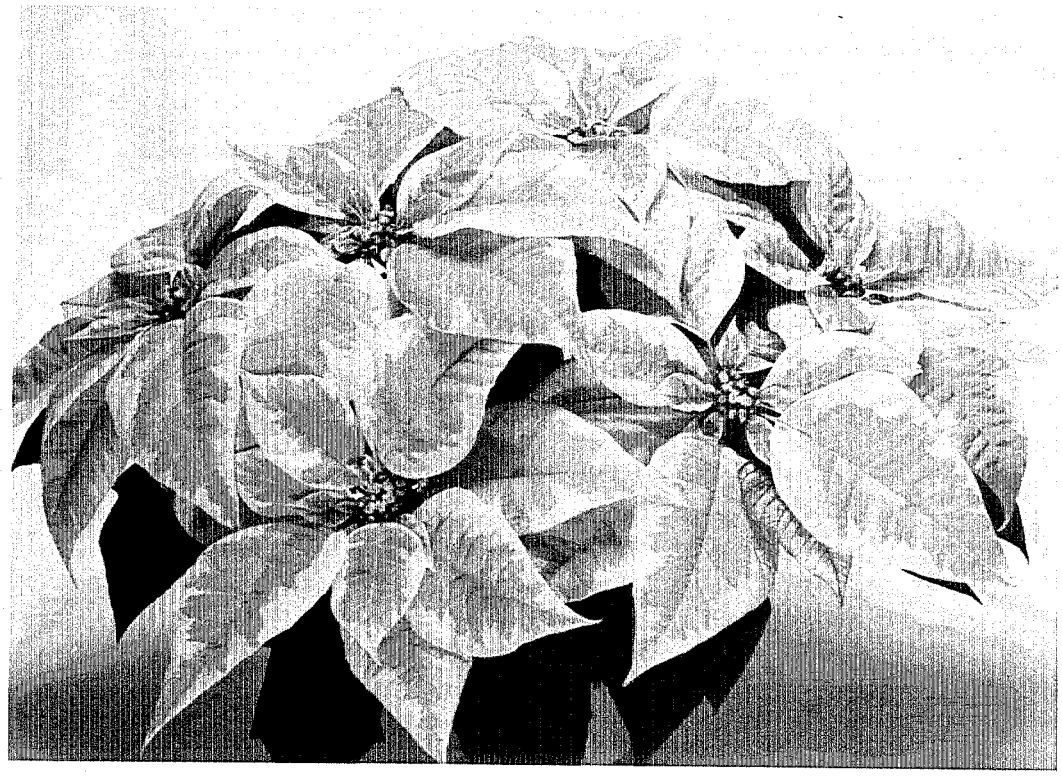

* * * * *